United States Patent

Ishikawa et al.

[11] Patent Number: 5,614,967
[45] Date of Patent: Mar. 25, 1997

[54] EYE MOVEMENT ANALYSIS SYSTEM

[75] Inventors: Norio Ishikawa; Hidehiro Hosaka, both of Tokyo, Japan

[73] Assignee: Nihon Kohden Corporation, Tokyo, Japan

[21] Appl. No.: 623,863

[22] Filed: Mar. 29, 1996

[30] Foreign Application Priority Data

Mar. 30, 1995 [JP] Japan .................................. 7-073227

[51] Int. Cl.⁶ ...................................................... A61B 3/14
[52] U.S. Cl. .......................................... 351/210; 351/209
[58] Field of Search ................................ 351/210, 209, 351/211, 205, 200

[56] References Cited

U.S. PATENT DOCUMENTS 5,196,873  3/1993  Yamanobe et al. ...................... 351/210

*Primary Examiner*—Hung X. Dang
*Attorney, Agent, or Firm*—Sughrue, Mion, Zinn, Macpeak & Seas

[57] ABSTRACT

An eye movement analysis system illuminates the surface of each eye, and calculates the movement of the eye from the image of the eye including the pupil and iris striation. The eye movement analysis system is made up of an image signal processor including a controller which calculates the movement of the eye as well as the respective positions of the center of the eye and the iris striation from the image of the eye and a RAM which holds the respective positions of the center of the eye and the iris striation, a display which displays the iris striation in different states before and after the positional analysis, and an operating section which stops changing the frame if the currently displayed iris striation is different from the previously specified iris striation.

3 Claims, 7 Drawing Sheets

POSITION ON FIRST FRAME

POSITION ON n-TH FRAME n-TH SCREEN (n+1)TH SCREEN

HORIZONTAL MOVEMENT

VERTICAL MOVEMENT

TORSIONAL MOVEMENT

EYE MOVEMENT ANALYSIS SYSTEM

BACKGROUND OF THE INVENTION

The present invention relates to an eye movement analysis system which measures the movement of eyes.

An eye movement analysis system (as disclosed in U.S. Pat. No. 5,196,873) which was devised by the inventor et al. of the present invention is already known. In this eye movement measuring system, a plurality of light sources that emit infrared rays are arranged around the pupil of each eye, and these light sources are blinked. The pupil and iris striations are photographed. Horizontal, vertical, and torsional components of the eye movement are calculated from variations in the respective positions of the center of the pupil and the iris striations, whereby the eye movement is analyzed.

FIG. 6 is a block diagram of the aforementioned eye movement analysis system. The eye movement analysis system comprises a plurality of light sources 60 arranged around the pupil of each eye (E), a video camera 61 for photographing the eye E, and an image pickup means consisting of a video control section 62 for controlling the video camera 61 and a synchronous illuminating circuit 63 for synchronizing the blinking action of the light source 60 with a video signal. These elements are integrated into a pair of goggles. The image pickup means is further provided with polarizing filters F1 and F2 for eliminating irregularly reflected unnecessary light. The eye is exposed to infrared rays emitted as a result of blinking the light sources 60, and iris striations, the pupil and its surrounding are photographed.

The thus picked up image of the eye is recorded using a VTR (video tape recorder) 64 via the video control section 62. A time base collector 65 synchronizes an image signal with a synchronizing signal of an image signal processor, thereby resulting in a synchronous image.

An image signal processor 66 comprises a control circuit 66a for controlling the overall system, an analog-to-digital converter 66b for converting an analog image signal into a digital image signal, a frame buffer 66c which consists of a RAM for storing an image signal for one frame, a binary-coding section 66d which converts the image signal into binary digits, an image recognition section 66e which calculates the coordinates of the pupil and the iris striation, a computing section 66f which calculates the horizontal, vertical, and torsional components of the eye movement on the basis of the thus obtained coordinates of the pupil and the iris striation, and memory 66g for storing the result of the calculation. The image signal processor 66 is connected to a keyboard 67 for setting data having a required number of frames, a display 68 for displaying an image of the eye and the result of the calculation, and a printer 69 for recording the result of the calculation as required. The control circuit 66a has a built-in ROM (not shown), and a control program block of the control circuit is provided with a built-in program which displays a specification frame (a window) so as to surround the pupil and the iris striation displayed on the screen when the pupil and the iris striation are specified. As a result of specifying the displayed pupil and iris striation using the window, their coordinates on the screen are automatically calculated.

With the above mentioned configuration, processing is executed on the basis of a flowchart shown in FIGS. 7 and 8 when the eye movement is analyzed by photographing the iris striation and the pupil of the eye. Specifically, a subject wears a pair of goggles on his/her face, these goggles comprising the light sources 60, the video camera 61, and the video control section 62. A shutter speed of the video camera, the time period during which the light sources 60 are illuminated, and illumination timing for synchronizing the time period with the opening action of the shutter, are set with the keyboard 67 (step S1). Then, each eye is photographed (step S2), and the video control section 62 adds a time code to a resultant image signal (step S3). The image signal is then output and recorded in the VTR 64 (step S4).

The required number of frames, for example, 30 frames, is set by way of the keyboard 67 (step S5). The image of the eye reproduced by the VTR 64 is frozen at its first frame until the image processor receives a control signal from the control circuit 66a (step S6).

The image signal output from the VTR 64 is synchronized with a synchronizing signal of the image signal processor 66 by means of the time base collector 65, whereupon the thus synchronized image signal is output (step S7). This eye image signal is then converted into a digital signal by the analog-to-digital converter 66b of the image signal processor 66 (step S8), and the digital image signal is stored in the frame buffer 66c (step S9).

If the number of frames is n=1 (the first frame) (step S10), a window is displayed on the screen of the display 68 together with the image of the eye (step S11). The pupil of the eye and the iris striation to be measured are manually or automatically specified (step S12). In this case, the specifying action is only required for one frame. Further, it is possible to keep track of the pupil and iris striation with increased accuracy if a plurality of iris striations are specified.

If it has been judged in step S10 that the number of frames is not n=1, the processing proceeds to step S13 which will be described later. The data read from the frame buffer 66c are converted into image data (brightness data), corresponding to the brightness and darkness of the image, by the binary-coding section 66d.

While the respective positions of the center of the eye and the iris striation are specified, an image recognition processing section 66e track the center of the eye (that is, the center of the pupil) and the iris striation, by recognizing and processing one frame of processing data comprising bright and dark information, that is, one frame of binary-coded data, as binary-coded brightness data. The coordinates of the eye center and the iris striation are then calculated (step S13). The result of this calculation is stored in the memory 66g (step S14).

If the number of frames is different from the value (for example, n=30) set in step S5 (step S15), frames are automatically fed (step S16). An image signal for the second frame is reproduced by the VTR 64, and the processing returns to step S7. The image signal is then analyzed through the above mentioned procedures, and the processing is repeated up to the set n-th frame.

In this way, after the processing up to the set n-th frame has been completed, variations with time of the coordinates of the center of the eye in both horizontal and vertical directions, and variations with time of a torsional angle, are calculated from each of analyzed data items with regard to the eye and iris striation. As a result, the movement of each eye is analyzed (step S17), and the movement is displayed on the display 68 (step S18). The movement is then output to the printer 69 (step S20), as required (step S19). The analysis of the eye movement is now terminated.

However, the above described conventional eye movement analysis system automatically analyzes the position of the eye up to the preset number of frames, which makes it impossible for an operator to check whether or not a previously specified target iris striation has been actually specified in an analyzing step in which sequentially input iris striations are automatically recognized. For this reason, analyzed data may include data on the position of an erroneous iris striation, which leads to decreased reliability of the result of the analysis.

SUMMARY OF THE INVENTION

The present invention is conceived in view of the foregoing problem in the prior art, and the object of the present invention is to provide a highly reliable eye movement analysis system capable of recognizing the position of an analyzed iris striation.

To this end, according to a first aspect, the present invention provides an eye movement analysis system which irradiates light to the center of each eye and its surrounding, and calculates the movement of the eye from an image of the eye, that is, an image of the pupil and iris striation obtained as a result of the reflection of the light, the improvement being characterized by comprising: image signal processing means provided with control means which calculates the position of the center of the eye and the position of the iris striation from the image of the eye and calculates the movement of the eye, and storage means which holds the calculated respective positions of the center of the eye and the iris striation; display means which displays the position of the iris striation in different states before and after the calculation of its position; and operating means for terminating the analysis of the next frame if the displayed iris striation is different from a previously specified iris striation.

According to a second aspect of the invention, in the eye movement analysis system of the first aspect, the display means displays the iris striation in different colors before and after the analysis of its position.

According to a third aspect of the invention, in either of the eye movement analysis systems of the first and second aspects of the invention, the display means blinks the iris striation obtained after the analysis of its position.

In the eye movement analysis system of the first aspect of the present invention, the control means of the image signal processing means calculates the respective positions of the pupil and the iris striation from the image of the eye. The movement of the eye is calculated on the basis of the position of the eye center and the position of the iris striation, and the thus calculated respective positions of the eye center and the iris striation are stored in the storage means. The display means displays the iris striation in different states before and after the calculation of its position. If the displayed iris striation of the eye is different from a previously specified target iris striation, the operating means does not carry out the analysis of the next frame.

In the eye movement analysis system of the second aspect of the present invention, the iris striations are displayed in different colors before and after the analysis of the positions.

In either of the eye movement analysis systems of the first and second aspects of the present invention, the iris striation obtained as a result of the analysis of the positions is displayed in a blinking manner.

DETAILED DESCRIPTION OF THE PREFERRED EMBODIMENTS

One preferred embodiment of the present invention will now be described referring to the accompanying drawings.

Figure 1:
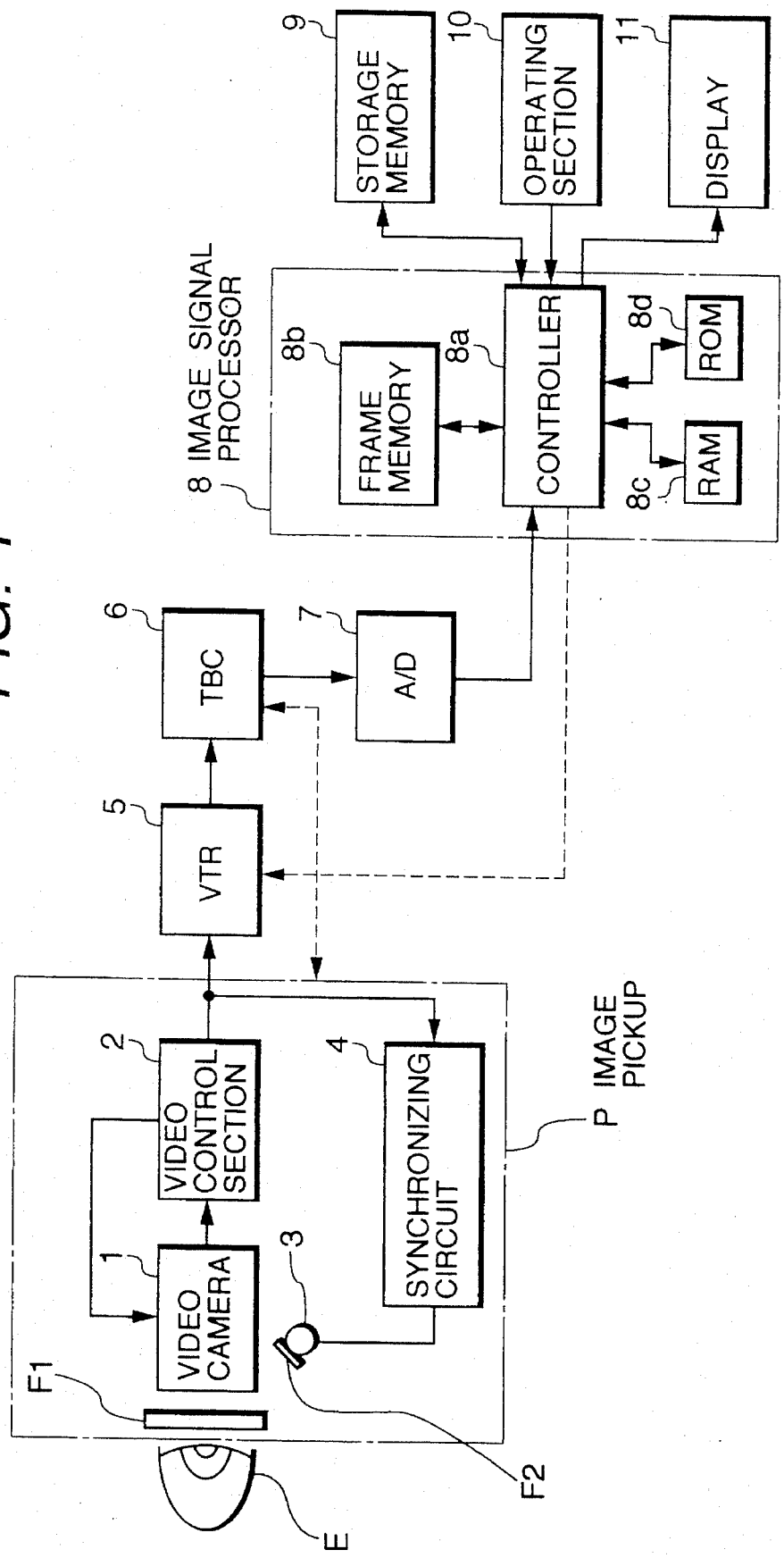
FIG. 1 is a block diagram showing the circuit configuration of an eye movement analysis system according to the present invention.
Figure 2:
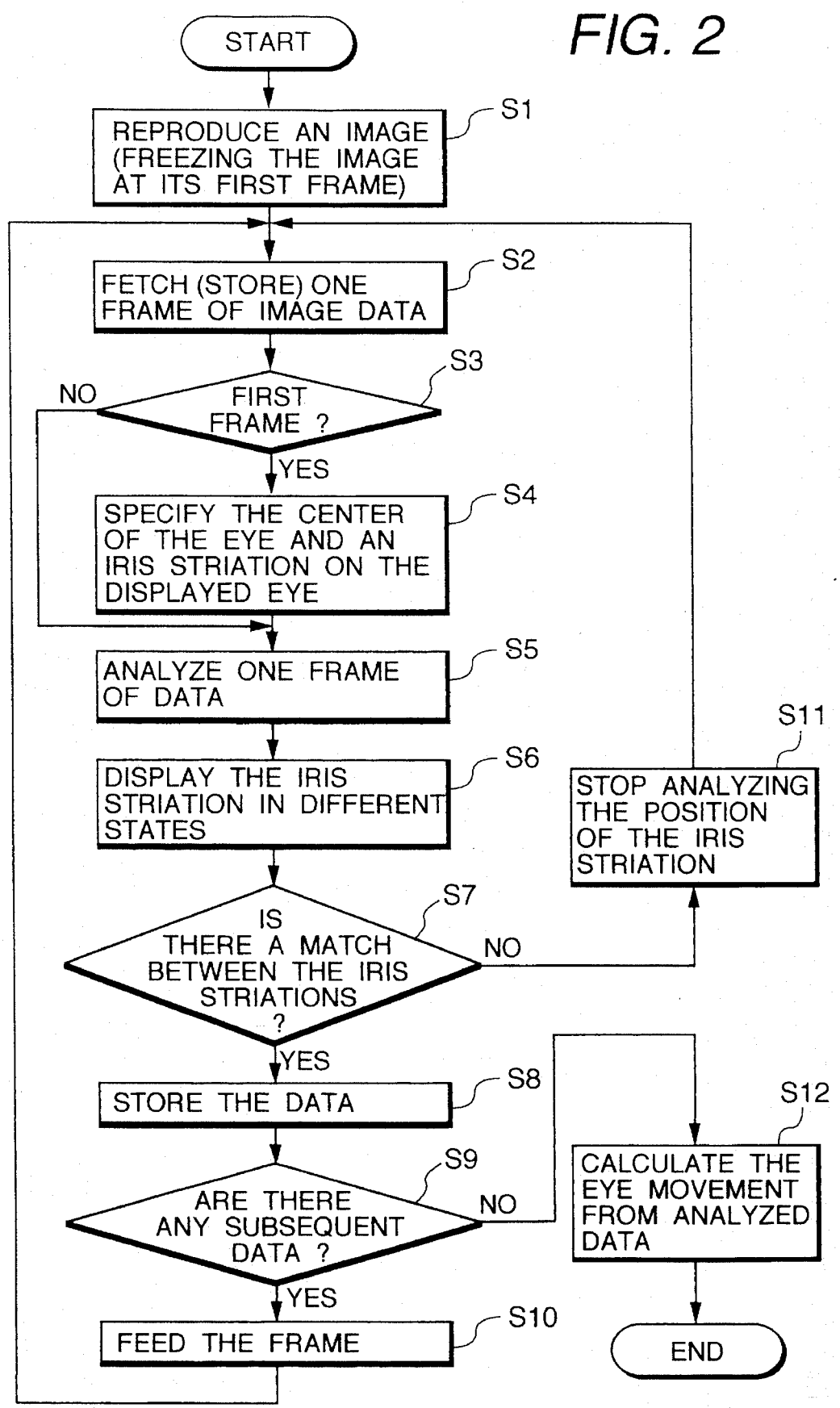
FIG. 2 is a flowchart showing processing operations of the eye movement analysis system according to the embodiment shown in FIG. 1.
Figure 3A:
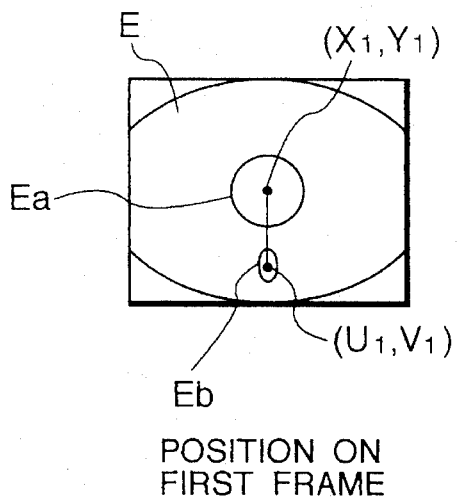
FIGS. 3A and 3B show variations in the respective positions of the pupil and an iris striation between different frames.
Figure 3B:
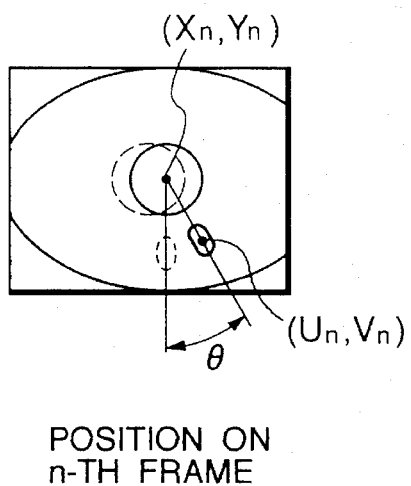
Figure 4A:
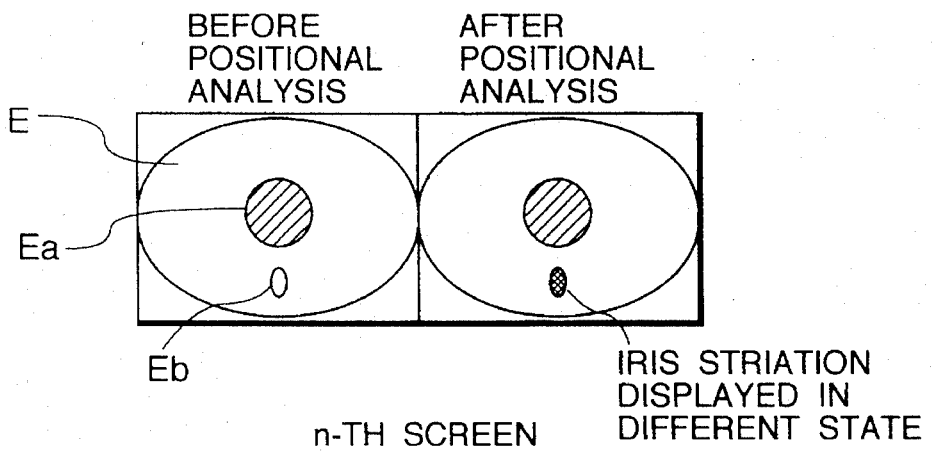
FIGS. 4A and 4B show displayed states of the iris striation before and after positional analysis according to the embodiment shown in FIG. 1.
Figure 4B:
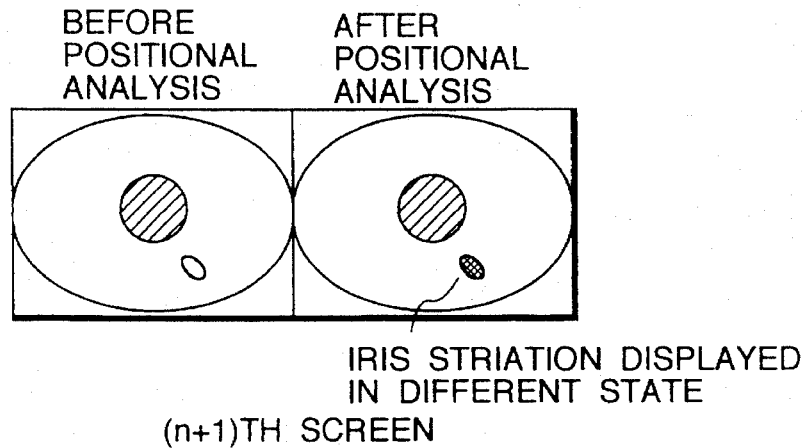
Figure 5A:
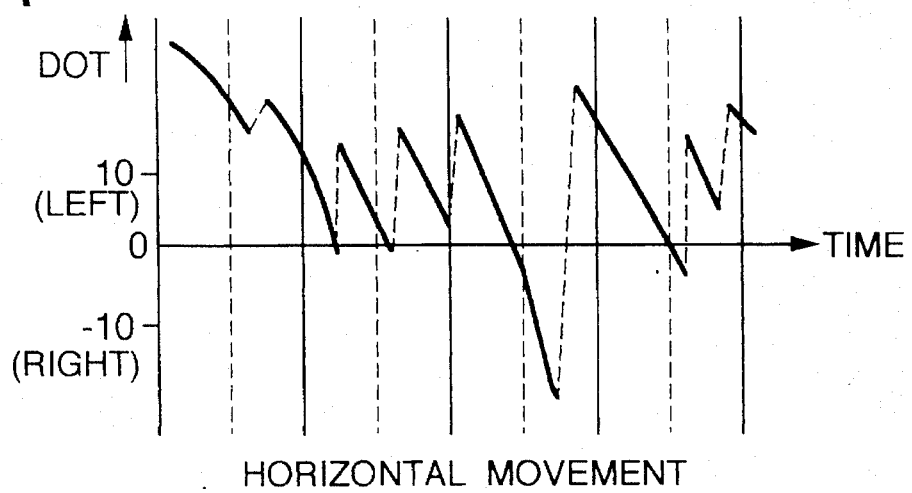
FIGS. 5A to 5C are plots showing the horizontal, vertical, and torsional components of the eye movement measured in the embodiment shown in FIG. 1.
Figure 5B:
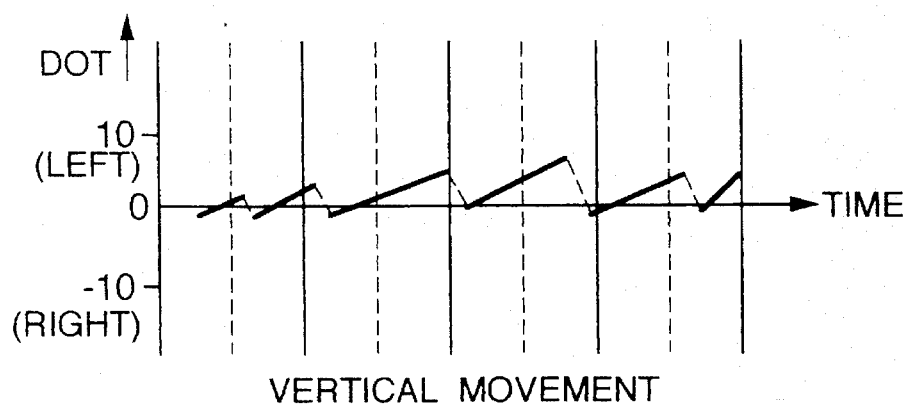
Figure 5C:
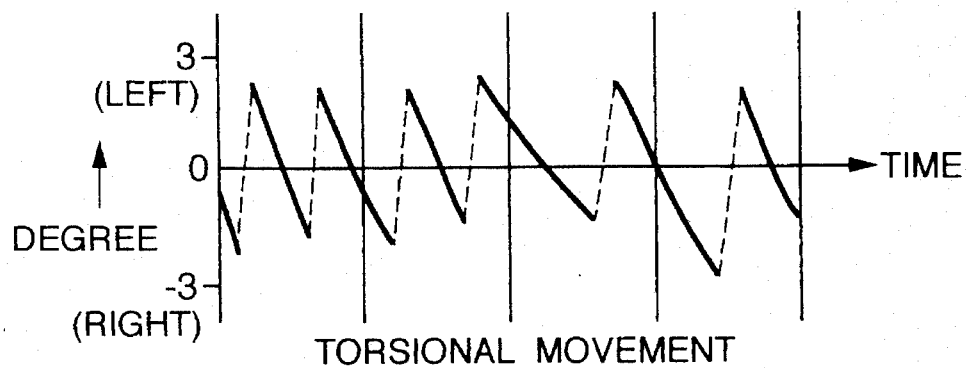

FIG. 1 is a block diagram showing the configuration of an eye movement analysis system according to one embodiment of the present invention. FIG. 2 is a flowchart showing processing procedures carried out by the eye movement analysis system shown in FIG. 1. FIGS. 3A and 3B are schematic representations showing variations in the respective positions of the pupil and an iris striation between different frames. FIGS. 4A and 4B are schematic representations showing the displayed states of the iris striation, according to the embodiment shown in FIG. 1, before and after the analysis of its position. FIGS. 5A to 5C are plots showing the horizontal, vertical, and torsional components of the analyzed movement of an eye.

FIG. 1 shows a video camera 1, a video control section 2 for controlling the speed of an electronic shutter of the video camera 1, light sources 3 which are made of, for example, an LED and emit infrared rays, and a synchronizing circuit 4 which blinks the light sources 3 in synchronism with an image signal from the video camera 1. Polarizing filters F1 and F2 eliminate irregularly reflected unnecessary light which makes an image of the iris striation dim when it is photographed. A VTR 5 records and reproduces a signal representing the image of the eye photographed by the video camera 1. It may be possible to use a digital recorder such as a laser disk, a mini-disk (MD), or a magneto-optical disk. An image pickup section P is made up of these elements, that is, the video camera 1, the video control section 2, the light sources 3, the synchronizing circuit 4, and the polarizing filters F1 and F2. As with the previously described conventional eye movement analysis system, it is possible to integrate these elements into a pair of goggles or the like. When being used, the pair of goggles are worn by the subject so as to be positioned close to the eyes E.

A time base collector circuit (TBC) 6 synchronizes a synchronizing signal of the VTR 5 with a synchronizing signal of an image signal processor which will be described later. An analog-to-digital converter 7 converts an analog image signal output from the TBC 6 into a digital image signal. If the previously mentioned digital recorder is used instead of the VTR 5, the analog-to-digital converter 7 will become unnecessary.

The aforementioned image signal processor 8 is made up of a controller 8a consisting of, for example, a CPU, a frame memory 8b consisting of, for example, a RAM which holds one frame of image data, an RAM 8c which temporarily holds preset data and processed data, and a ROM 8d having a previously stored control program.

Storage memory 9 consisting of, for example, an IC card with battery backup and a hard disk, holds the data on the eye movement calculated by the image signal processor 8.

The specification of the respective positions of the pupil and the iris striation of the image of the eye and the setting of a variety of data are carried out through an operating section 10 consisting of, for example, a keyboard. A display 11 consisting of, for example, a liquid crystal display, displays data with regard to the image and movement of the eye.

With the above configuration, the processing of the eye movement will be described on the basis of the flowchart shown in FIG. 2. In this case, the image pickup section P is worn by the subject, and the eyes of the subject are previously photographed and recorded in the VTR 5.

The image of the eye recorded in the VTR 5 is reproduced, and the thus reproduced image is synchronized with the video camera 1 by the TBC 6. The analog-to-digital converter 7 converts an eye image signal into a digital signal, and the thus converted digital signal is delivered to the image signal processor 8. The digital image is then displayed on the screen of the display 11. However, the digital image is frozen at its first frame, under control of the controller 8a (step S1).

One frame of image data received by the image signal processor 8 are stored in the frame memory 8b (step S2). The image data read from this frame memory 8b are subjected to a decision as to whether or not the number of frames is 1 (step S3). During the course of reading the image data from the frame memory 8b, the data on the pupil and iris striation of the eye are coded into image data having bright and dark information, that is, brightness data.

Figure 6:
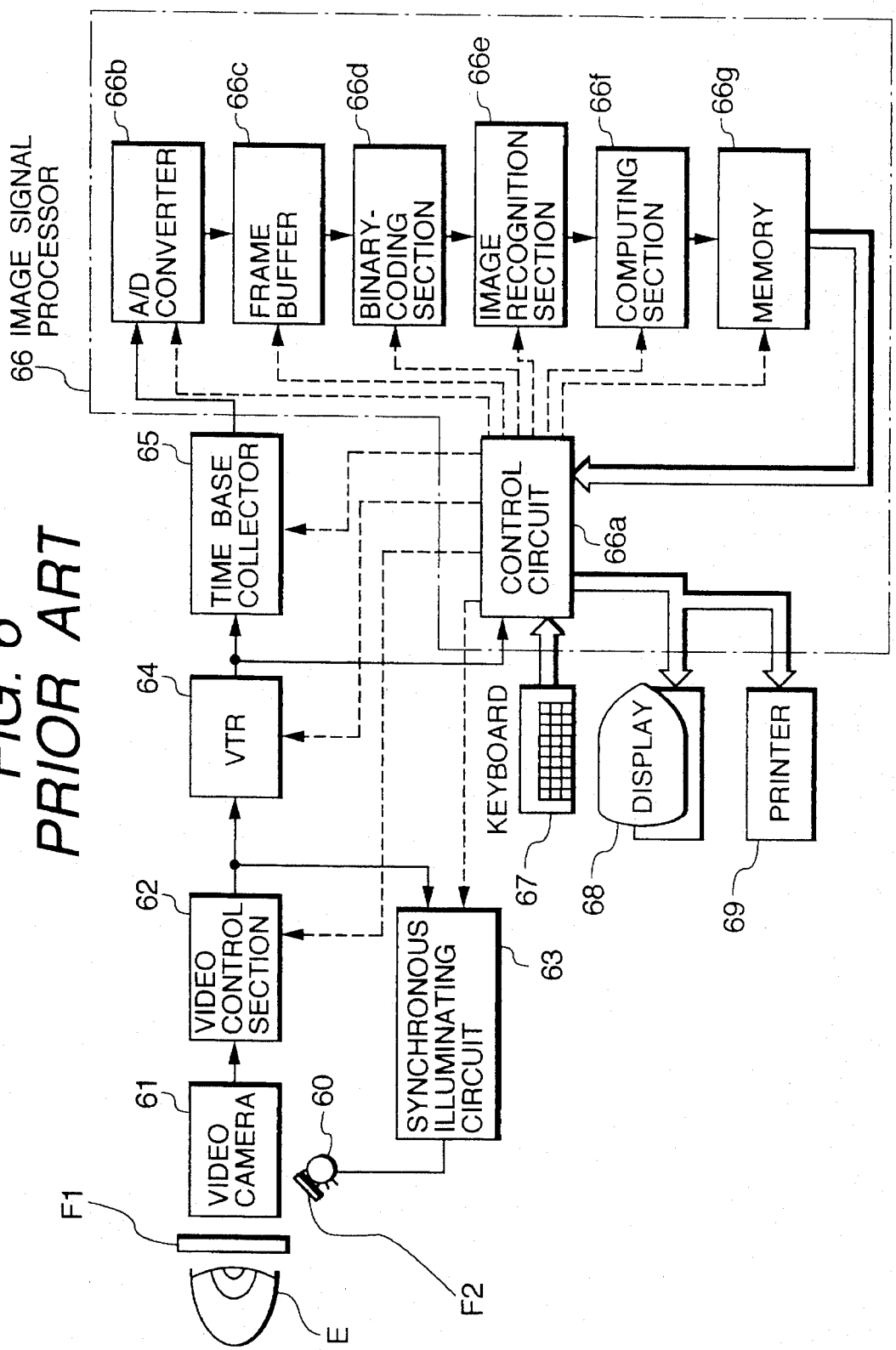
FIG. 6 is a block diagram showing the configuration of a conventional eye movement analysis system.
Figure 7:
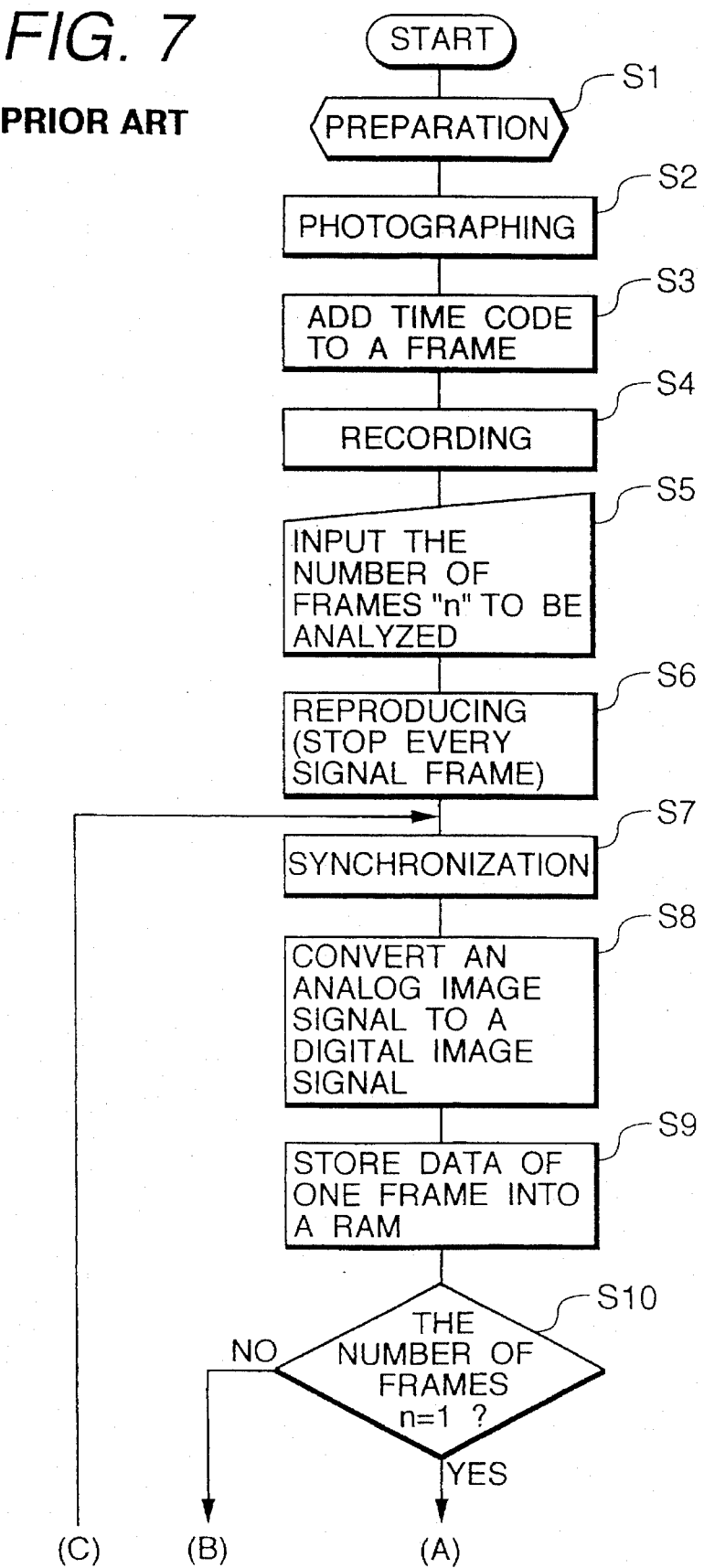
FIG. 7 is a flowchart showing the processing associated with the circuit configuration shown in FIG. 6.
Figure 8:
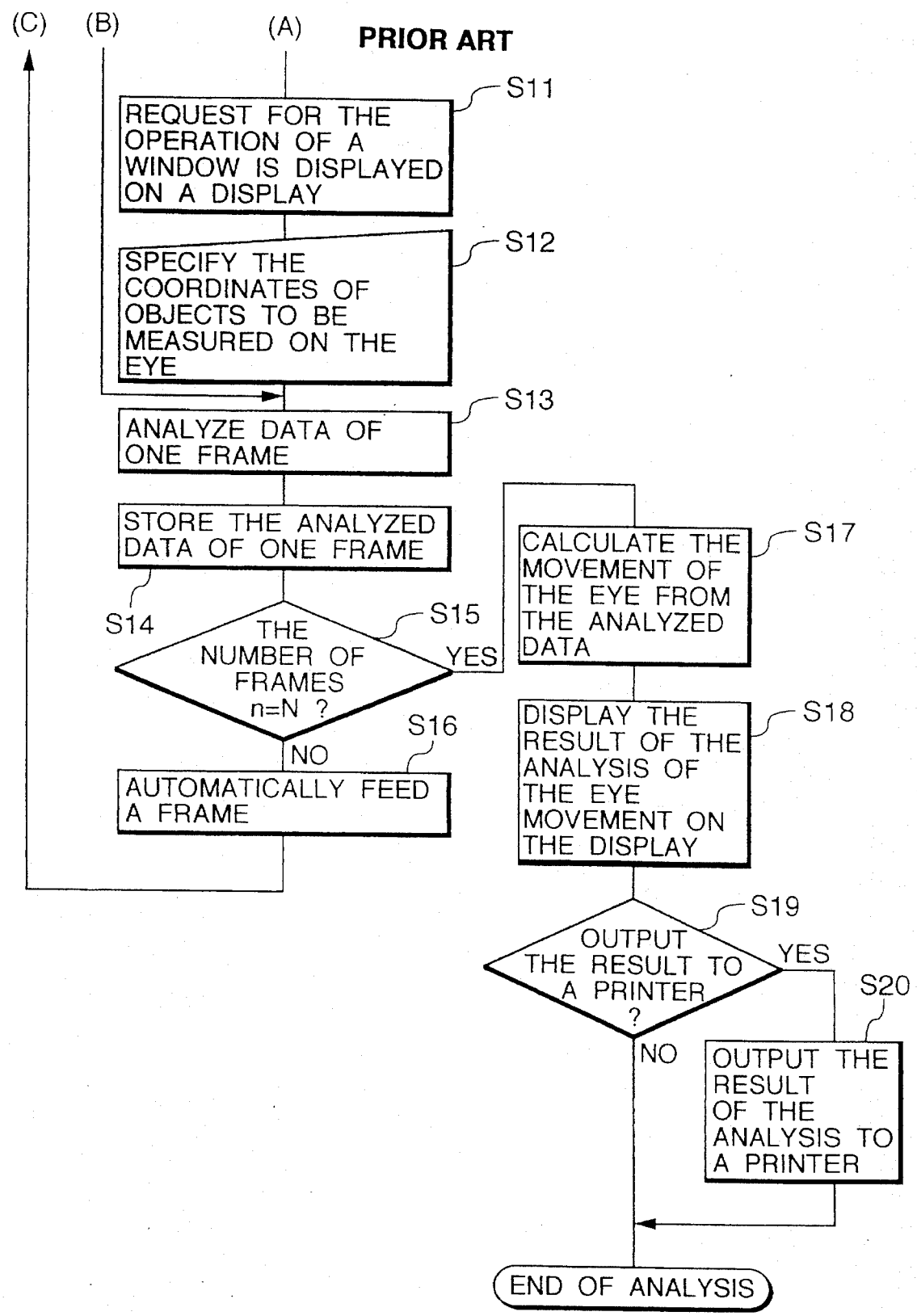
FIG. 8 is a flowchart showing the processing continued from FIG. 7.

If it has been judged in step S3 that the number of frames is "1", the image of the eye is displayed, and the center of the eye (pupil) and the iris striation are manually or automatically specified through the operating section 10 (step S4). As has been described with regard to the conventional eye movement analysis system shown in FIG. 6, the center of the eye and the iris striation are specified by surrounding the pupil of the eye and the iris striation, both being displayed on the screen, by, for example, a variable-size window (a rectangular frame). Further, it is only essential for the pupil and the iris striation to be specified with regard to the first frame. In other words, the first frame of the image of the eye provides a reference for the analysis of variations in the positions of the center of the eye and the iris striation. For this reason, it becomes necessary to specify their positions. With regard to frames following the first frame, the respective positions of the center of the eye and the iris striation are automatically calculated with reference to their positions previously specified for the first frame.

The respective coordinates of the eye and the iris striation are calculated from the specified respective positions of the center of the eye and the iris striation (step S5). If it has been judged in step S3 that the number of frames is not "1", the respective coordinates of the center of the current eye and the center of the current iris striation are calculated from the respective coordinates of the center of the eye and the center of the iris striation obtained in step S5. For the iris striation of each of frames following the first frame, a torsional angle, which will be described later, will be calculated in addition to the calculation of the coordinates of the center of the iris striation.

FIGS. 3A and 3B show the coordinates of the center of the eye (that is, the center of the pupil) and the center of the iris striation. FIG. 3A shows the coordinates of the center of the eye, that is, $(X_1, Y_1)$, and the coordinates of the center of the iris striation, that is, $(U_1, V_1)$ with regard to the first frame. On the other hand, FIG. 3B shows the coordinates of the center of the eye, that is, $(Xn, Yn)$, and the coordinates of the center of the iris striation, $(Un, Vn)$ with regard to the n-th frame. The dotted line shown in FIG. 3B denotes the respective positions of the pupil and the iris striation of the first frame shown in FIG. 3A.

Horizontal and vertical displacements of the coordinates of the center of the pupil of each frame are calculated with reference to the coordinates of the center of the pupil by subtraction, that is, $(Xn-X_1)$ and $(Yn-Y_1)$. If the iris striation of the first frame has moved (rotated) to such a position as shown in FIG. 3B at the time of the n-th frame, the torsional component of the movement of the iris striation can be calculated by the following expression, assuming that an angle with respect to the normal extending from the center of the pupil Ea is $\theta$.

$$\theta = \tan^{-1}(Vn-Yn)/(Un-Xn) - \tan^{-1}(V_1-Y_1)/(U_1-X_1)$$

If a number of iris striations, for example, a number of iris striations "M", are specified for the first frame, a mean angle $\theta$ among $\theta_1$ to $\theta_m$ of the iris striations is obtained. The mean angle $\theta$ can be obtained from $(\theta_1+\theta_2+\ldots+\theta_m)/M$.

On the assumption that variations in the respective coordinates of the center of the eye and the center of the iris striation and variations in the torsional angle with regard to the frames following the first frame are calculated with reference to the respective coordinates of the center of the eye and the center of the iris striation of the first frame, and that the thus obtained variations are plotted, it becomes possible to display variations in the horizontal, vertical, and torsional directions of the eye.

Turning again to FIG. 2, the coordinates of the center of the eye and the center of the iris striation and a torsional angle of the iris striation are calculated in step S5, and the eye and the iris striation to be tracked are displayed on the screen of the display 11. The operator can visually check the position of the iris striation on the screen (step S6). At this time, the current iris striation is displayed in a color which is different from the color of the iris striation before it undergoes the positional analysis. Alternatively, the iris striation before undergoing the positional analysis is displayed without being blinked, and the iris striation that has undergone the positional analysis is blinked, or it is blinked in different colors.

FIGS. 4A and 4B show examples of screens in the case where iris striations Eb of the n-th and (n+1)th frames are colored after they have undergone the positional analysis. FIG. 4A shows a screen for the n-th frame that illustrates the iris striation before and after the positional analysis, and FIG. 4B shows a screen for the (n+1)th frame that illustrates the iris striation before and after the positional analysis. As can be seen from these drawings, as a result of displaying the iris striation Eb in different colors before and after the positional analysis, it is possible for the operator to acknowledge at glance that the iris striation has finished being subjected to the positional analysis.

The operator judges whether or not the iris striation to be tracked is located at the correct position by observing the image of the eye displayed on the screen of the display 11 (step S7). If the iris striation is located at the correct position, the image data are stored in the RAM 8c (step S8). In this case, if the iris striation is located at the correct position, it is also possible to proceed to the next processing by operating, for example, an appropriate key on the operating section 10. However, it may be possible to arrange the system in such a way that data on the correct iris striation are automatically input, unless the system receives some other input within one second such as an entry associated with an error key of the operating section 10. Such an arrangement makes the key operation of the operator unnecessary, which in turn allows the operator to concentrate on monitoring the screen.

If it has been judged in step S7 that the iris striation is not located at an intended tracking position, the operator stops feeding the frames of the image of the eye displayed on the display 11 by operating, for example, an error key via the operating section 10 (step S11). In this case, the processing returns to step S2, and the above mentioned processing is executed again.

After the image data is stored at step S8, it is judged whether there are next frame data (step S9). In case that there are frame data, the controller 8a sends a control signal to the VTR 5 to feed a frame (step S10), and the process is returned to step S2 to take the next frame data and to carry out the above process.

If it has been judged in step S9 that there is no subsequent frame data, the control section 8a reads the analyzed frame data stored in the RAM 8c. Variations with time in the horizontal and vertical components of the data on the coordinates of the center of the eye (pupil) are calculated. Variations with time in the torsional angle of the data on the coordinates of the center of the iris striation are calculated, whereby the movement of the eye is obtained (step S12). The thus obtained eye movement is output to the screen or stored in the storage memory 9. The analysis of the eye movement is now completed.

The result of the measurement of the eye movement obtained in step S12 can be displayed in the form of a plot as shown in FIGS. 5A–5C. FIG. 5A shows the horizontal movement of the eye with respect to the eye center (pupil), FIG. 5B shows the vertical movement of the eye, and FIG. 5C shows the torsional movement of the eye.

Although the displayed state of only the iris striation is changed before and after its positional analysis in the above described embodiment, it may be possible to change the displayed state of the pupil of the eye before and after the positional analysis. It is also possible to display the pupil in black before it undergoes the positional analysis and to display the same in light blue after the positional analysis has been completed. Further, although only one iris striation is used in the above embodiment, a plurality of iris striations may be used in the eye movement analysis system of the present invention.

As has been described above, according to the eye movement analysis systems of the first to third aspects of the present invention, it is possible to check the iris striation frame by frame while it is displayed in different states. Hence, resultant data errors are reduced, thereby resulting in improved reliability of the result of the analysis of the eye movement.

What is claimed is:

1. An eye movement analysis system which analyzes movement of each of eyes on the basis of a position of the center of a pupil and a position of at least one iris striation, both being included in a recorded image of the eye, the system comprising:

image signal processing means provided with
  control means which calculates the respective positions of the pupil and the iris striation by tracking the pupil and iris striation that are specified on the eye image every time a frame of the image is fed, and
  storage means which holds the thus calculated respective positions of the center of the eye and the iris striation;

display means which displays the iris striation located at the calculated position and the iris striation before being subjected to the calculation in different manners; and operating means for stopping feeding the frame of the image if the iris striation displayed after the calculation is different from the iris striation before being subjected to the calculation.

2. An eye movement analysis system as claimed in claim 1, wherein the display means displays the iris striation that has been subjected to the calculation and the iris striation before being subjected to the calculation in different colors.

3. An eye movement analysis system as claimed in claim 1, wherein the display means blinks the iris striation that has been subjected to the calculation.

\* \* \* \* \*